United States Patent [19]

Frey et al.

[11] Patent Number: 5,689,014

[45] Date of Patent: Nov. 18, 1997

[54] INTEGRATED PROCESS FOR PRODUCING DIISOPROPYL ETHER AND AN ISOPROPYL TERTIARY ALKYL ETHER

[75] Inventors: Stanley J. Frey, Palatine; Robert J. Schmidt, Barrington; Terry L. Marker, Warrenville; Richard E. Marinangeli, Arlington Heights, all of Ill.

[73] Assignee: UOP, Des Plaines, Ill.

[21] Appl. No.: 539,577

[22] Filed: Oct. 5, 1995

[51] Int. Cl.$^6$ .................................................. C07C 41/05
[52] U.S. Cl. ................................. 568/697; 568/698
[58] Field of Search ...................... 568/697, 698

[56] References Cited

U.S. PATENT DOCUMENTS

| | | | |
|---|---|---|---|
| 4,393,250 | 7/1983 | Gottlieb et al. | 568/697 |
| 5,011,506 | 4/1991 | Harandi et al. | 44/447 |
| 5,324,866 | 6/1994 | Marker et al. | 568/697 |
| 5,371,301 | 12/1994 | Marker et al. | 568/694 |

FOREIGN PATENT DOCUMENTS

WO 92/08683  5/1992  WIPO.

*Primary Examiner*—Marianne M. Cintins
*Assistant Examiner*—Dwayne C. Jones
*Attorney, Agent, or Firm*—Thomas K. McBride; Eugene I. Snyder; Maryann Maas

[57] ABSTRACT

A highly integrated process for concurrently producing diisopropyl ether and an isopropyl tertiary alkyl ether has been developed. In a first reactor, propylene and water are reacted to form isopropyl alcohol, a portion of which is further reacted to form diisopropyl ether. After removing unreacted propylene, the effluent of the first reactor is separated into an ether rich stream, a water rich stream and an alcohol rich stream. The alcohol rich stream and isobutylene, isoamylene or a mixture thereof are reacted to form an isopropyl tertiary alkyl ether in a second reactor. The water present in the alcohol rich stream also reacts with the iso-olefin to form tertiary alcohol. The effluent from the second reactor is water washed to produce an oxygenate product stream and an aqueous alcohol recycle stream. Some tertiary alcohol is recycled to the first reactor where it is reacted with propylene to form additional isopropyl tertiary alkyl ether. The isopropyl tertiary alkyl ether and some tertiary alcohol is collected along with the diisopropyl ether in the mixed oxygenate product stream from the water wash.

14 Claims, 1 Drawing Sheet

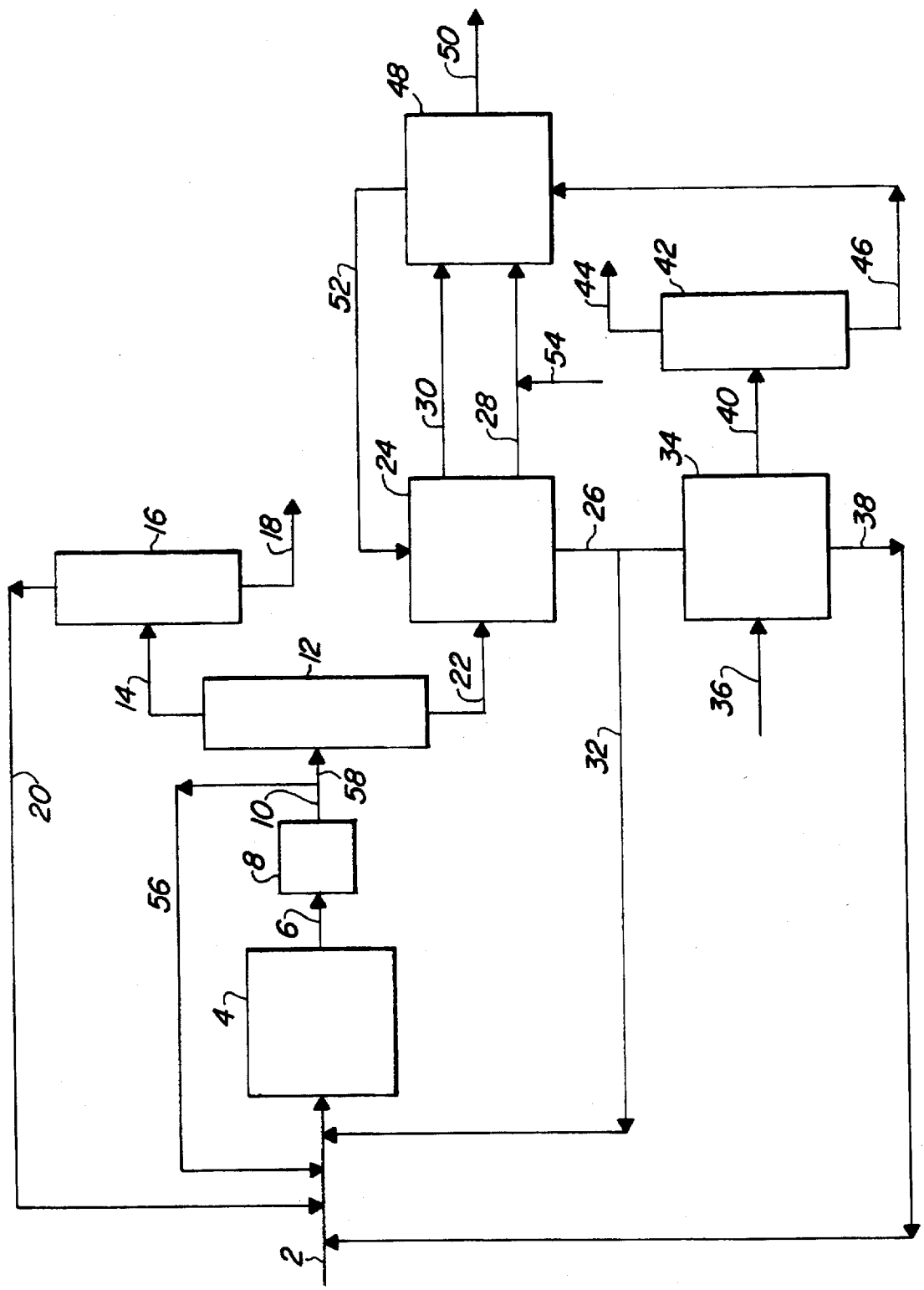

5,689,014

INTEGRATED PROCESS FOR PRODUCING DIISOPROPYL ETHER AND AN ISOPROPYL TERTIARY ALKYL ETHER

BACKGROUND OF THE INVENTION

As tetraethyl lead is phased out, oxygenates have become more important in the petroleum refining industry as a source of gasoline octane boosters. The most common oxygenates for this purpose are the dialkyl ethers, especially those in the $C_5$ to $C_8$ range. One example of such a dialkyl ether is diisopropyl ether which is in the boiling range of gasoline and has a high blending octane number of 105 and a blending Reid vapor pressure of 5. Furthermore, one reactant generally used in the formation of diisopropyl ether is propylene which is a by-product commonly available in refineries. The preparation of diisopropyl ether from propylene proceeds by two sequential reactions: (1) where propylene is first hydrated to isopropyl alcohol followed by reaction of the alcohol with the olefin, or (2) by a single bimolecular dehydration reaction of the alcohol (Williamson synthesis). Two more examples of desirable dialkyl ethers are isopropyl tertiary butyl ether and isopropyl tertiary amyl ether. Isopropyl tertiary butyl ether has a blending octane number of 113 and a blending Reid vapor pressure of 2.5. Isopropyl tertiary amyl ether has a blending octane number of 110 and a blending Reid vapor pressure of 2. These ethers may be produced through olefin etherification by reacting isopropyl alcohol with isobutylene and isoamylene, respectively, or by reacting propylene with tertiary butyl alcohol or tertiary amyl alcohol, respectively.

The preparation of diisopropyl ether from propylene and water is well known and numerous processes exist in the art such as U.S. Pat. No. 5,324,866 and U.S. Pat. No. 5,371,301. The production of isopropyl tertiary butyl ether and isopropyl tertiary amyl ether from reacting isopropyl alcohol with butylene and amylene is also known as demonstrated in U.S. Pat. No. 5,011,506 and U.S. Pat. No. 4,393,250.

Furthermore, U.S. Pat. No. 5,011,506 and WO 92/08683 disclose a process where excess isopropyl alcohol formed in a diisopropyl ether production reactor is separated, dewatered, and routed to an isopropyl tertiary alkyl ether production reactor where the isopropyl alcohol is reacted with iso-olefins to produce the isopropyl tertiary alkyl ethers. The isopropyl alcohol is dewatered using the iso-olefins feedstream as an extractant. The integration of the diisopropyl ether production process and the isopropyl tertiary alkyl ether production process occurs entirely prior to the isopropyl tertiary alkyl ether production reactor; there is no further integration of the processes downstream.

Applicants, however, are the first to realize that 1) it is not necessary to dewater the isopropyl alcohol before using it as a reactant in an isopropyl tertiary alkyl ether production reactor and the alcohol stream may contain as much as 20 mass % water, and 2) a higher degree of integration between a diisopropyl ether production process and an isopropyl tertiary alkyl ether production process is possible. Eliminating the dewatering requirement of the isopropyl alcohol actually increases the yield of oxygenates since tertiary alcohols are produced from water reacting with an iso-olefin in the isopropyl tertiary alkyl ether production reactor. Some of the tertiary alcohol is recycled to the diisopropyl ether reactor to react with propylene and form additional amounts of isopropyl tertiary alkyl ether and some of the tertiary alcohol is collected in the product stream. The higher degree of integration allows for the advantage of a single product stream of mixed oxygenates that does not have one discrete boiling point which would affect the shape of a gasoline distillation curve.

SUMMARY OF THE INVENTION

The purpose of the invention is to provide a highly integrated process for concurrently producing diisopropyl ether and an isopropyl tertiary alkyl ether. In a first reactor, propylene and water are reacted to form isopropyl alcohol, a portion of which is further reacted to form diisopropyl ether. After removing unreacted propylene, the effluent of the first reactor is separated into an ether rich stream, a water rich stream and an alcohol rich stream. The alcohol rich stream and isobutylene, isoamylene or a mixture thereof are reacted to form an isopropyl tertiary alkyl ether in a second reactor. The water present in the alcohol rich stream also reacts with the iso-olefin to form tertiary alcohol. Unreacted iso-olefins and inert compounds are then removed from the second reactor effluent. The effluent from the second reactor is water washed to produce an oxygenate product stream and an aqueous alcohol recycle stream. Some tertiary alcohol is ultimately recycled to the first reactor where it is reacted with propylene to form additional isopropyl tertiary alkyl ether. The isopropyl tertiary alkyl ether and some tertiary alcohol is collected along with the diisopropyl ether in the mixed oxygenate product stream from the water wash. A more specific embodiment of the invention is one where catalyst degradation products are removed from the first reactor effluent before further processing.

BRIEF DESCRIPTION OF THE DRAWING

FIG. 1 is a schematic representation of the preferred embodiment of the invention. The drawing has been simplified by the deletion of a large number of pieces of apparatus customarily employed in processes of this nature which are not specifically required to illustrate the performance of the subject invention.

DETAILED DESCRIPTION OF THE INVENTION

The invention involves a highly integrated ether production process where at least diisopropyl ether and an isopropyl tertiary alkyl ether are concurrently produced. The integration of the processes involves introducing water and excess isopropyl alcohol from a diisopropyl ether reactor to an isopropyl tertiary alkyl ether reactor, concurrently water washing the effluents from both of the reactors to form a single mixed oxygenate product stream, and recycling some tertiary alcohols formed in the isopropyl tertiary alkyl ether reactor to the diisopropyl ether reactor to provide additional ether production.

The process begins with water and a hydrocarbon feedstock containing propylene being introduced to a first reactor containing an acidic catalyst. The operating conditions of the first reactor include pressures of about 100 to about 1500 psig, preferably from about 700 to about 1000 psig, and temperatures of about 130° to about 180° C., preferably from about 135° to about 160° C. It is common to slowly increase the operating temperature as the catalyst ages. Suitable water to olefin mole ratios include from about 0.1:1 to about 0.8:1, preferably about 0.5:1. The propylene-containing hydrocarbon feedstock may be a refinery $C_3$ hydrocarbon stream and will most likely be a mixture of propylene and propane. The propylene-containing hydrocarbon feedstock should contain at least about 50 mass % propylene and preferably from about 70 to about 80 mass % propylene. Suitable sources for the propylene-containing hydrocarbon feedstock include, but are not limited to, gas plant off-gas containing propylene, naphtha cracker off-gas containing light olefins, propylene from a propane dehydrogenation process, and refinery fluidized catalytic cracked (FCC) propane/propylene streams.

Up to about four additional streams may also be introduced to the first reactor. One such stream is an aqueous recycle stream containing mainly water with some isopropyl alcohol from a water separator located downstream in a second reaction zone. A second such stream is a recycle stream containing water, isopropyl alcohol, and a tertiary alcohol which is either tertiary butyl alcohol, tertiary amyl alcohol, or a mixture thereof from another downstream separator. Separated and recycled unreacted propylene may also be introduced to the first reactor. Finally, a portion of the first reactor effluent after acid is removed may be recycled to increase conversion of propylene and alcohol to ether and to control the temperature in the reactor. The details of the generation of these recycle streams will be discussed below as the particular units involved are discussed.

The acidic catalyst contained in the first reactor may be any of those commonly used for a diisopropyl ether production process including acidic ion exchange resins, acidic zeolites, and supported heteropoly acids. The most preferred are the acidic ion exchange resins including sulfonated cation exchange resins such as sulfonated polystyrene resins and sulfonated styrene/divinylbenzene co-polymers. An example of a suitable sulfonated styrene/divinylbenzene co-polymer catalyst is Purolite CT-175 sold by Purolite; two more examples of preferred catalysts include Amberlyst® 36 and Amberlyst® 16. These sulfonated cation exchange resins are common in the art and do not require discussion here. For reference, see, U.S. Pat. No. 5,371,301, G.B. 1,176,620, and U.S. Pat. No. 4,182,914. Halogenated strong acid ion exchange resins such as those described in U.S. Pat. No. 4,705,808, U.S. Pat. No. 4,269,943, and U.S. Pat. No. 3,256,250 may also be used. Suitable zeolitic catalysts are described in U.S. Pat. No. 5,011,506, and suitable supported heteropoly acids are described in U.S. Pat. No. 3,996,298 and U.S. Pat. No. 3,758,615.

As the propylene and water contact the catalyst, the hydration reaction takes place and isopropyl alcohol is formed. As isopropyl alcohol and propylene contact the catalyst, an etherification reaction takes place and diisopropyl ether is formed. Bimolecular dehydration of the isopropyl alcohol may also take place to form diisopropyl ether, but it is less preferred due to the increased consumption of isopropyl alcohol as compared to the etherification reaction. As recycled tertiary alcohol and propylene contact the catalyst, an etherification reaction takes place and isopropyl tertiary alkyl ether is formed. For example, as tertiary butyl alcohol and propylene contact the catalyst, isopropyl tertiary butyl ether is formed; likewise, as tertiary amyl alcohol and propylene contact the catalyst, isopropyl tertiary amyl ether is formed. Therefore, the first reactor effluent is a mixture of water, propylene, isopropyl alcohol, tertiary alcohol, diisopropyl ether, and isopropyl tertiary alkyl ether.

Catalyst degradation products may also be present in the first reactor effluent. An example of a particular acidic ion exchange resin catalyst degradation product is acid. Since catalyst deactivation may be accelerated by recycling a portion of the reactor effluent which contains catalyst degradation products to the reactor, the reactor effluent may be treated to remove the catalyst degradation products. For example, where the catalyst degradation product is acid, the effluent may be passed through an acid removal zone which contains solid particles capable of removing acid from the reactor effluent. Such solid particles include alkaline metal oxides, basic ion exchange resins, basic organically-bridged polysilsesquioxane particles, or any other strongly basic inorganic compounds with reasonable thermal stability, considering the reactor effluent will be at temperatures from about 130° C. to about 160° C. Activated carbon is also suitable. Other degradation products may be removed using similar commonly known means.

At least a portion of the first reactor effluent, which may have been processed to remove catalyst degradation products, is recycled to the first reactor to react the propylene and isopropyl alcohol to form diisopropyl ether and to control the temperature in the reactor. Suitable recycle ratios range from about 2:1 to about 10:1 and preferably about 5:1. The remainder of the first reactor effluent is first treated to remove light materials and then separated into an ether enriched stream, an alcohol enriched stream, and a water enriched stream. The removal of light material is accomplished in a first light ends fractionation zone where compounds such as propylene and propane are removed. The first light ends fractionation zone may be operated at a temperature of about 80° C. and a pressure of about 235 psig. The separated light compounds such as propylene and propane may then be passed to a propylene/propane fractionation column where propane and propylene are separated into two streams. The propane enriched stream may be collected, and the propylene enriched stream may be recycled to the reactor. The recycled propylene enriched stream may contain as little as 50 mass % propylene, preferably from about 70 to about 85 mass % propylene, thereby eliminating the need for the expensive equipment required to obtain high purity propylene. The separated heavier compounds such as water, alcohols, and ethers are passed from the first light ends fractionation zone to a separator.

The separator is a fractionation column operating at from about 50° C. to about 150° C. and from about 25 to about 125 psig which separates the heavier compounds into an ether enriched stream containing diisopropyl ether and isopropyl tertiary alkyl ether, a water enriched stream, and an alcohol enriched stream containing isopropyl alcohol and tertiary alcohol. Note that without further drying, the alcohol enriched stream contains from 5 to about 20 mass % water. A portion of the alcohol enriched stream is recycled to the first reactor to increase the conversion of alcohols, including isopropyl alcohol and tertiary alcohol, to ethers and a portion of the alcohol enriched stream is passed to a second reactor to form isopropyl tertiary alkyl ether.

The operating conditions of the second reactor include pressures of about 100 to about 300 psig, preferably from about 100 to about 175 psig, and temperatures of about 30° C. to about 100° C., preferably from about 40° C. to about 80° C. It is common to slowly increase the operating temperature as the catalyst ages. A feed stream containing isobutylene, isoamylene, or a mixture thereof is also introduced to the second reactor. Suitable isopropyl alcohol to iso-olefin mole ratios include from about 3:1 to about 1.5:1. The iso-olefin-containing stream may be a refinery $C_4$ and/or $C_5$ hydrocarbon stream and will most likely be a mixture of isomeric $C_4$ and/or $C_5$ olefins and paraffins. Suitable sources for the iso-olefin-containing hydrocarbon feedstock include, but are not limited to, iso-olefins from a $C_4/C_5$ dehydrogenation process and refinery fluidized catalytic cracked $C_4/C_5$ streams. These streams typically also contain a significant amount of inert compounds.

The catalyst used in the second reactor may be any of those discussed above as suitable for use in the first reactor.

The preferred catalyst is a macroporous acid form sulfonic ion exchange resin such as the sulfonated styrene-divinyl benzene resin described in U.S. Pat. No. 2,922,822. Other suitable resins include copolymers of sulfonyl fluorovinyl ether, fluorocarbons, and $SiO_2$-modified cation exchangers as described in U.S. Pat. No. 3,784,399, U.S. Pat. No. 3,849,243, and U.S. Pat. No. 4,751,343. Particularly suitable and preferred catalysts are sold under the designations Amberlyst® 35 and Amberlyst® 36 by Rohm and Haas. It is further contemplated that suitable catalysts include metal-containing resins which contain one or more metals from the sub-groups VI, VII or VIII of the Periodic Table such as chromium, tungsten, palladium, nickel, platinum, or iron as described in U.S. Pat. No. 4,330,679. Other catalysts include acidic shape-selective acidic zeolites or clays. Suitable zeolites may be of intermediate pore size such as ZSM-5 or of a large pore size such as zeolite-Y, zeolite beta, and ZSM-12. These zeolites and additional suitable zeolites are discussed in U.S. Pat. No. 5,011,506.

Because of the high water content in the alcohol enriched stream that is passed to the second reactor, it is likely that a two-phase system will occur. Therefore, a water separator may be incorporated prior to the second reactor. Both the iso-olefin containing feed stream and the alcohol enriched stream are introduced to the water separator where two phases readily separate. The aqueous phase, which contains a small amount of alcohol, is recycled to the first reactor and the organic phase, which contains the iso-olefins, most of the alcohol, and is saturated with water, is passed to the second reactor.

As the iso-olefin and isopropyl alcohol contact the catalyst in the second reactor, an etherification reaction takes place and isopropyl tertiary alkyl ether is formed. If the iso-olefin is isobutylene, then isopropyl tertiary butyl ether is formed, and if the iso-olefin is isoamylene, then isopropyl tertiary amyl ether is formed. If both isobutylene and isoamylene are present, both isopropyl tertiary butyl ether and isopropyl tertiary amyl ether are formed. For ease of understanding, the term "isopropyl tertiary alkyl ether" is used herein to refer to isopropyl tertiary butyl ether, isopropyl tertiary amyl ether, or the mixture thereof, whichever is present. The water present will also react with the iso-olefins to produce tertiary alcohol. If the iso-olefin is isobutylene, then tertiary butyl alcohol is formed, and if the iso-olefin is isoamylene, then tertiary amyl alcohol is formed. If both isobutylene and isoamylene are present, both tertiary butyl alcohol and tertiary amyl alcohol are formed. For ease of understanding, the term "tertiary alcohol" is used herein to refer to tertiary butyl alcohol, tertiary amyl alcohol, or the mixture thereof, whichever is present. It is not expected for the tertiary butyl alcohol or the tertiary amyl alcohol to react with the isobutylene or isoamylene in the second reactor since the tertiary butyl alcohol and tertiary amyl alcohol are sterically hindered. Therefore, the second reactor effluent contains a mixture of iso-olefin, isopropyl alcohol, tertiary alcohol, isopropyl tertiary alkyl ether, and water.

The second reactor effluent is passed to a second light ends fractionation zone for removal of compounds such as iso-olefins and other inert hydrocarbons typically containing about 4 or 5 carbon atoms that are often present in the iso-olefin feed to the second reactor. The second light ends fractionation zone may be operated at a temperature of about 60° C. and a pressure of about 70 psig. The separated light compounds may be passed to other processes in a refinery and the remainder is passed to a water wash unit.

At least three streams are introduced to the water wash unit: 1) the separated heavier compounds such as water, alcohols, and ethers from the second light ends fractionation zone, 2) the ether rich stream from the separator, and 3) the water rich stream from the separator. Additional water may be added to the water wash unit as necessary. The water wash unit is operated at a temperature of about 40° C. to about 80° C. and a pressure of about 150 to about 200 psig. Two streams are produced: an alcohol and water stream and a mixed oxygenate stream. The alcohol and water stream will contain water, isopropyl alcohol, and tertiary alcohol. The mixed oxygenate stream will contain diisopropyl ether, isopropyl tertiary alkyl ether, and tertiary alcohol. Since tertiary butyl alcohol is very water soluble, all of the tertiary butyl alcohol present will wash into the water and alcohol stream. However, since tertiary amyl alcohol is not very water soluble, most of any tertiary amyl alcohol present will wash into the mixed oxygenate stream. It is expected that the mixed oxygenate stream will contain greater than 96 mass % oxygenated high octane blending components. The alcohol and water stream containing isopropyl alcohol and tertiary alcohol is recycled to the separator and the mixed oxygenate stream is collected.

Without intending any limitation of the scope of the present invention and as merely illustrative, the invention is explained below in specific terms as applied to a specific embodiment of the invention which is based on a design for a commercial scale unit. Referring to the figure, a 70 mass % propylene-30 mass% propane feed 2, a water, isopropyl alcohol, tertiary alcohol, propylene, propane, and diisopropyl ether containing recycle 56, an isopropyl alcohol-water azeotrope containing stream 32, and a propylene-containing recycle 20 are combined and introduced to a first reaction zone 4 which contains Amberlyst® 36 catalyst. Reaction zone 4 is operated at 150° C. and 1000 psig. In reaction zone 4, the hydrolysis of propylene is catalyzed and isopropyl alcohol is formed, the isopropyl alcohol is then catalytically reacted with propylene to form diisopropyl ether. Tertiary alcohol is also catalytically reacted with propylene to form isopropyl tertiary alkyl ether. Concurrently, the high temperature of the reaction zone and the presence of water cause $SO_3$ to split off from the acidic ion exchange resin catalyst. Due to the presence of water, the $SO_3$ forms $H_2SO_4$ which is carried into the reaction mixture. Other oxo acids of sulfur such as $HSO_3^-$ or $HSO_4^-$ may be formed, but for ease of understanding, only $H_2SO_4$ will be discussed. Reaction zone effluent 6 contains propylene, propane, water, isopropyl alcohol, tertiary alcohol, diisopropyl ether, isopropyl tertiary alkyl ether, and $H_2SO_4$, and is cooled to 80° C. via heat exchangers (not shown) before being passed to acid removal unit 8 which contains Amberlite® IRA-68 basic ion exchange resin and is operated at 80° C. and 975 psig. As fluid reaction zone effluent 6 contacts the Amberlite® IRA-68 basic ion exchange resin, $SO_4^=$ or $HSO_4^-$ from the reaction zone effluent is exchanged for 2 $OH^-$ or $OH^-$ from the resin which neutralizes the $H^+$, thereby resulting in an $H_2SO_4$-depleted stream 10. $H_2SO_4$-depleted stream 10 is divided into two portions: one portion, stream 56, is recycled to reaction zone 4, and one portion, stream 58, is passed to a first light ends recovery unit 12. The recycle rate is about 5:1.

Fractionation in first light ends recovery unit 12 at 80° C. and 235 psig results in a propane and propylene stream 14 which is passed to a propylene-propane fractionation column 16, and a water, isopropyl alcohol, tertiary alcohol, diisopropyl ether, and isopropyl tertiary alkyl ether stream 22 which is passed to a separator column 24. In propylene-propane fractionation column 16, propane and propylene stream 14 is separated into a propane enriched stream 18 which is collected, and a propylene enriched stream 20 which contains about 85 mass % propylene and is recycled to reaction zone 4. In separator column 24 the water, isopropyl alcohol, tertiary alcohol, diisopropyl ether, and isopropyl tertiary alkyl ether stream 22 is fractionated at 150° C. and 125 psig to form a water enriched stream 28, an aqueous alcohol stream 26, and an ether enriched stream 30. Aqueous alcohol stream 26 contains about 20 mass % water and about 70 mass% alcohol. A portion of aqueous alcohol stream 26 is recycled to reaction zone 4 via line 32, and water stream 28 and ether enriched stream 30 is passed to a water wash unit 48.

Aqueous alcohol stream 26 and a 7.5 mass % isobutylene, 12.5 mass% isoamylene feed 36 is passed to a second reaction zone 34. In second reaction zone 34 two phases readily separate and an aqueous recycle stream 38 is recycled to first reaction zone 4. A reactor in second reaction zone 34 contains Amberlyst® 35 catalyst and is operated at 60° C. and 150 psig. In second reaction zone 34 the etherification of isobutylene and isoamylene with isopropyl alcohol is catalyzed and isopropyl tertiary butyl ether and isopropyl tertiary amyl ether are formed. The water present in aqueous alcohol stream 26 is also catalytically reacted with the isobutylene and isoamylene to form tertiary butyl alcohol and tertiary amyl alcohol. Due to the lower operating temperature of second reaction zone 34, it is not expected that significant amounts of acid from the catalyst will enter the reaction mixture. Second reaction zone effluent 40 contains water, isobutylene, isoamylene, isopropyl alcohol, tertiary butyl alcohol, tertiary amyl alcohol, isopropyl tertiary butyl ether, and isopropyl tertiary amyl ether. Second reaction zone effluent 40 is directed to a second light ends fractionation zone 42 operating at 60° C. and 70 psig. Fractionation of second reaction zone effluent 40 in second light ends fractionation zone 42 results in an inert compounds, isobutylene, and isoamylene stream 44 and a water, isopropyl alcohol, tertiary butyl alcohol, tertiary amyl alcohol, isopropyl tertiary butyl ether, and isopropyl tertiary amyl ether stream 46.

Stream 46 and streams 28 and 30 discussed earlier are introduced to water wash unit 48. A water feed 54 may be combined with stream 28 when additional water is necessary. A mixed oxygenate product stream 50 containing at least 96 mass % mixed oxygenates, i.e., diisopropyl ether, isopropyl tertiary butyl ether, isopropyl tertiary amyl ether, and tertiary amyl alcohol is withdrawn from water wash unit 48 and collected. An aqueous alcohol stream 52 containing water, isopropyl alcohol, tertiary butyl alcohol, and tertiary alcohol is withdrawn from water wash unit 48 and recycled to separator 24.

What is claimed is:

1. An integrated process for producing diisopropyl ether and an isopropyl tertiary alkyl ether comprising:
   a. reacting propylene, water, a tertiary alcohol, and isopropyl alcohol in the presence of an acidic catalyst to afford a first reaction zone effluent;
   b. recycling a portion of the first reaction zone effluent to step (a) and removing propylene from the remainder to afford a propylene-depleted stream;
   c. separating the propylene-depleted stream into an ether enriched stream, an alcohol enriched stream, and a water enriched stream;
   d. reacting the alcohol enriched stream with isobutylene, isoamylene, or a mixture thereof present in a feed stream further containing inert material, in the presence of an acidic catalyst to afford a second reaction zone effluent and an aqueous stream;
   e. recycling the aqueous stream to step (a);
   f. removing the inert material, and isobutylene, isoamylene, or the mixture thereof from the second reaction zone effluent to afford an iso-olefin depleted stream;
   g. water washing a mixture of the iso-olefin depleted stream, the ether enriched stream, and the water enriched stream to afford an aqueous alcohol stream and an oxygenate stream;
   h. recycling the aqueous alcohol stream to step (c); and
   i. collecting the oxygenate stream.

2. The process of claim 1 where the alcohol enriched stream contains from about 5 to about 20 mass % water.

3. The process of claim 1 where the acidic catalyst in step (a) is selected from the group consisting of acidic ion exchange resins, acidic zeolites, and supported heteropoly acids.

4. The process of claim 1 where the acidic catalyst in step (a) is an acidic ion exchange resin.

5. The process of claim 1 where the acidic catalyst in step (d) is selected from the group consisting of acidic ion exchange resins, metal containing resins, acidic zeolites, clays, copolymers of sulfonyl fluorovinyl ether, fluorocarbons and $SiO_2$-modified cation exchangers.

6. The process of claim 1 further comprising removing catalyst degradation products from the first reaction zone effluent prior to recycling.

7. The process of claim 1 further comprising removing acid from the first reaction zone effluent prior to recycling.

8. An integrated process for producing diisopropyl ether and an isopropyl tertiary alkyl ether comprising:
   a) reacting
      i. propylene and water,
      ii. an alcohol enriched recycle stream containing water, isopropyl alcohol, and tertiary alcohol, from a separator, and
      iii. a recycle stream containing isopropyl alcohol and water, from a second reaction zone,
   in a first reaction zone in the presence of an acidic catalyst to produce a first reaction zone effluent containing propylene, water, isopropyl alcohol, diisopropyl ether, tertiary alcohol, and isopropyl tertiary alkyl ether;
   b) recycling a portion of the first reaction zone effluent to the first reaction zone and removing the propylene from the remainder to produce a stream containing water, isopropyl alcohol, diisopropyl ether, tertiary alcohol, and isopropyl tertiary alkyl ether;
   c) separating a mixture of the stream containing water, isopropyl alcohol, diisopropyl ether, tertiary alcohol, and isopropyl tertiary alkyl ether and a recycle stream from a water wash unit containing isopropyl alcohol, tertiary alcohol, and water in a separator to produce an ether enriched stream containing diisopropyl ether and isopropyl tertiary alkyl ether, an alcohol enriched stream containing water, isopropyl alcohol, and tertiary alcohol, and a water enriched stream;
   d) recycling a portion of the alcohol enriched stream to the first reaction zone;
   e) reacting the water and isopropyl alcohol present in a portion of the alcohol enriched stream with isobutylene, isoamylene, or a mixture thereof present in a feed stream further containing inert material, in a second reaction zone in the presence of an acidic catalyst to produce a second reaction zone effluent containing isobutylene, isoamylene, or the mixture thereof, water, isopropyl alcohol, tertiary alcohol, isopropyl tertiary alkyl ether, and inert material, and a stream containing water and isopropyl alcohol;

f) recycling the stream containing water and isopropyl alcohol to the first reaction zone;

g) removing the inert material, and isobutylene, isoamylene, or the mixture thereof from the second reaction zone effluent to produce a stream containing water, isopropyl alcohol, tertiary alcohol and isopropyl tertiary alkyl ether;

h) water washing a mixture of the ether enriched stream, the water enriched stream, and the stream containing water, isopropyl alcohol, tertiary alcohol and isopropyl tertiary alkyl ether to produce a stream containing isopropyl alcohol, tertiary alcohol, and water, and a product stream containing diisopropyl ether, isopropyl tertiary alkyl ether and tertiary alcohol; and i) recycling the stream containing isopropyl alcohol, tertiary alcohol, and water from the water wash to the separator.

9. The process of claim 8 where the alcohol enriched stream containing water, isopropyl alcohol, and tertiary alcohol of step (c) contains from about 5 to about 20 mass % water.

10. The process of claim 8 where the acidic catalyst in the first reaction zone is selected from the group consisting of acidic ion exchange resins, acidic zeolites, and supported heteropoly acids.

11. The process of claim 8, where the acidic catalyst in the first reaction zone is an acidic ion exchange resin.

12. The process of claim 8 where the acidic catalyst in the second reaction zone is selected from the group consisting of acidic ion exchange resins, metal containing resins, acidic zeolites, clays, copolymers of sulfonyl fluorovinyl ether, fluorocarbons and $SiO_2$-modified cation exchangers.

13. The process of claim 8, further comprising where the first reaction zone effluent additionally contains catalyst degradation products which are removed prior to recycling.

14. The process of claim 8, further comprising where the first reaction zone effluent additionally contains acid which is removed prior to recycling.

* * * * *